United States Patent [19]

Turk et al.

[11] Patent Number: 5,687,885

[45] Date of Patent: Nov. 18, 1997

[54] DISPENSING CONTAINER AND SLIDING CAP ASSEMBLY

[75] Inventors: Frederick J. Turk, St. Paul; Malcolm W. Wilcox, Woodbury; Thomas W. Martin, Maplewood, all of Minn.

[73] Assignee: Minnesota Mining and Manufacturing Co., St. Paul, Minn.

[21] Appl. No.: 547,595

[22] Filed: Oct. 24, 1995

[51] Int. Cl.$^6$ ................................... B65D 47/00
[52] U.S. Cl. ................ 222/512; 215/322; 220/347; 220/351; 222/137; 222/561
[58] Field of Search ................ 222/94, 137, 512, 222/542, 561, 562; 215/322; 220/345, 346, 347, 351, 378

[56] References Cited

U.S. PATENT DOCUMENTS

| | | | |
|---|---|---|---|
| 886,925 | 5/1908 | Betts et al. | 215/322 |
| 1,349,511 | 8/1920 | Kandlbinder | 215/322 X |
| 1,713,043 | 5/1929 | Fullerton . | |
| 2,033,256 | 3/1936 | Schacher | 222/512 X |
| 2,050,809 | 8/1936 | Ruetz | 222/512 X |
| 2,091,217 | 8/1937 | Ruetz | 222/512 X |
| 2,436,297 | 2/1948 | Guarnaschelli | 215/322 |
| 2,595,000 | 4/1952 | Ruetz | 222/561 X |
| 2,657,837 | 11/1953 | Bernhardt | 222/561 |
| 2,731,177 | 1/1956 | Ruetz | 222/561 X |
| 2,943,771 | 7/1960 | Driscoll | 222/512 |
| 3,199,749 | 8/1965 | Driscoll | 222/561 X |
| 3,422,997 | 1/1969 | Anderson | 215/322 X |
| 3,506,157 | 4/1970 | Dukess | 222/94 |
| 4,538,920 | 9/1985 | Drake | 222/137 X |
| 4,570,826 | 2/1986 | Fattori | 222/511 X |
| 4,583,665 | 4/1986 | Barriac | 222/83 |
| 4,771,919 | 9/1988 | Ernst | 222/134 |
| 4,869,399 | 9/1989 | Dubach | 222/83 |
| 4,964,539 | 10/1990 | Mueller | 222/94 |
| 4,974,756 | 12/1990 | Pearson et al. | 222/562 |
| 4,989,758 | 2/1991 | Keller | 222/137 |
| 5,115,949 | 5/1992 | Rosenthal | 222/512 X |
| 5,236,108 | 8/1993 | House | 222/137 X |
| 5,405,034 | 4/1995 | Mittel, Jr. | 215/322 |

FOREIGN PATENT DOCUMENTS

| | | |
|---|---|---|
| 772838 | 11/1934 | France . |
| 443066 | 2/1936 | United Kingdom . |
| 499845 | 4/1937 | United Kingdom . |
| 465717 | 5/1937 | United Kingdom . |
| 468549 | 7/1937 | United Kingdom . |

OTHER PUBLICATIONS

International Search Report for PCT/US96/09025.
Brochure for Imprint™ 2:5 Single Phase Technique from 3M Dental Product Division, copyright 1991.

Primary Examiner—Kevin P. Shaver
Attorney, Agent, or Firm—Gary L. Griswold; Walter N. Kirn; James D. Christoff

[57] ABSTRACT

A dispensing container, such as a double-barrel cartridge used in dispensing dental material, matingly receives a sliding cap that maintains a seal between material in the barrels and the atmosphere. The cap includes a body and a gasket within the body, and the cap also includes a cam portion that shifts the body slightly away from an outlet of the container as the cap is moved toward a closed position to seal the container. Once the cap is in a fully closed position, the cam portion enables the body to shift somewhat closer to the container outlet in order to increase the compression of the gasket between the body and the outlet. Optionally, an orienting section is provided for insuring that the cap is coupled to the container in only one certain orientation, so that the likelihood of cross-contamination of material within the barrels due to residual material on the gasket is substantially reduced.

15 Claims, 2 Drawing Sheets

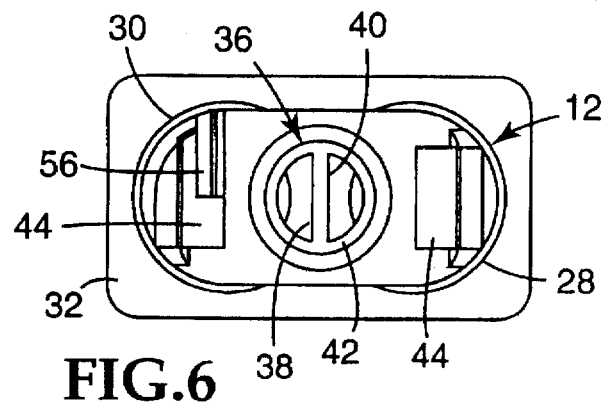
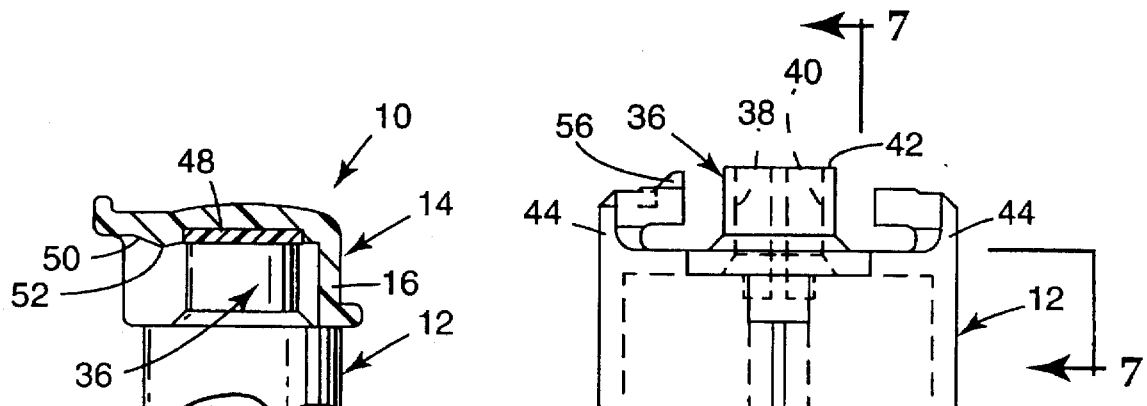
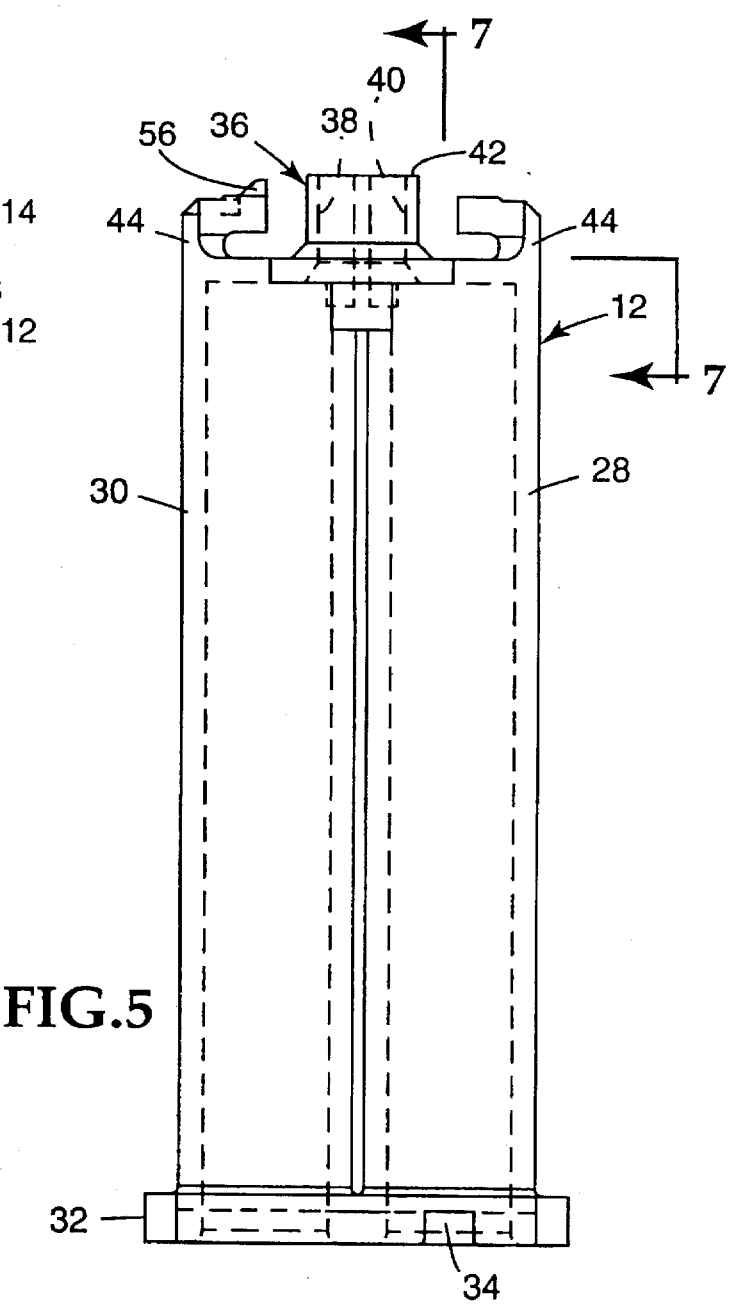

DISPENSING CONTAINER AND SLIDING CAP ASSEMBLY

BACKGROUND OF THE INVENTION

1. Field of the Invention

This invention relates to an assembly that includes a dispensing container having at least one outlet opening, and a cap that slides across each outlet opening as the cap is coupled or uncoupled from the container.

2. Description of the Related Art

Certain types of dispensing containers have been used with a cap that slides across an outlet opening of the container as the cap is coupled or uncoupled from the container. For example, U.S. Pat. Nos. 1,349,511 and 2,436,297 illustrate caps having one or more aprons with a curved lip. As the cap is slid onto the bottle, the curved lip engages a lower edge of a collar surrounding the bottle opening to serve as a coupler for releasably connecting the cap to the bottle.

The bottle cap shown in U.S. Pat. No. 2,436,297 also includes a washer to help seal the outlet opening of the bottle. The lip of the apron includes three curved indentations that extend toward the washer. As the cap is slid across the outlet opening to couple the cap to the bottle, the indentations serve to wedge the washer between the top of the cap and the outer surface of the bottle surrounding the opening in an attempt to seal the opening.

Unfortunately, the bottle and cap that are described in U.S. Pat. No. 2,436,297 are not entirely satisfactory because a substantial amount of friction is exerted on the washer due to the raised indentations as the cap is moved toward a closed position. If, for example, the washer is made of a material having relatively lithe tear strength, the material may rupture as the washer slides over the opening. Once ruptured, the washer may fail to present an effective seal between the contents of the bottle and the atmosphere.

Certain dispensing containers have double barrels that are useful for storing different reactive components that, once dispensed, are mixed together to form a desired composition. As an example, a double barrel dispensing syringe for dispensing dental impressioning material may hold a catalyst component in one chamber and a base component in another chamber. Portions of each impressioning component are simultaneously dispensed for immediate mixing such that measuring of the separate components is unnecessary.

One example of a double barrel dispensing syringe is described in U.S. Pat. No. 4,538,920 which is assigned to the assignee of the present invention. The syringe has two interconnected plungers for simultaneously dispensing proportioned amounts of component from each barrel of a disposable cartridge. An exit conduit is releasably connected to the syringe and has a plurality of helical mixing elements so that the components are thoroughly mixed once discharged from the exit conduit and mixing by hand may be avoided.

Typically, only a portion of the components are dispensed at any one time from the barrel chambers of the syringe shown in U.S. Pat. No. 4,538,920, and it is often desirable to keep the side-by-side outlets of the syringe covered between dispensing operations in order to prevent undue hardening or drying of the components in the barrels. In the past, certain dispensing syringes have been provided with a "twist-on" cap having flanges that releasably lock into recesses next to the two outlets of the syringe as the cap is turned approximately 90 degrees relative to the syringe. The cap carries an internal seal that covers both of the outlets when coupled to the syringe.

However, many conventional "twist-on" caps for double barrel syringes may contribute to cross-contamination of remaining components within the chambers. For example, if a small quantity of a component of one chamber is deposited on the seal within the rotatable cap mentioned above, the component may contact and react with the component in the other barrel as the cap is re-coupled to the cartridge after an initial use. Although the amount of reacted material and the resulting cross-contamination may be relatively small compared to the amount of components remaining within the chambers, such cross-contamination may result in a certain amount of polymerization that might hinder passage of the components along the tortuous path presented by the helical mixing elements.

Users of double barrel syringes are often provided with instructions that indicate that good results are attained when the exit conduit with the helical mixing elements is left connected to the container after use and the cap is not re-used. In this manner, mixed material within the exit conduit hardens and provides a seal that is often more satisfactory than a seal that would be established by re-use of conventional caps. Immediately prior to the next use, the exit conduit is disposed of and a new exit conduit is connected to the container in its place.

While the used exit conduit may provide a satisfactory seal between uses when the dispensing syringe is used to dispense silicone dental impressioning material, such an exit conduit may not provide a satisfactory seal when the syringe is used to dispense other material such as a water-based curable material, since a better seal is often necessary to prevent leakage and premature curing of water-based material. Another problem associated with leaving the exit conduit coupled to the dispensing cartridge between uses arises in instances where the exit conduit is partially placed within the patient's oral cavity during a dispensing operation. When the exit conduit is used within the patient's oral cavity, the exit conduit should be immediately disposed of after use in order to help prevent the spread of any infectious disease to the next patient.

U.S. Pat. No. 5,236,108 (assigned to the assignee of the present invention) describes a double barrel dispensing cartridge or container assembly with a peel-off seal that is initially located between outlets of the container and a slidable cap. Once the cap is removed and the seal is disposed of, the cap, if reattached, does not tightly engage the outlets but instead can only be loosely coupled to the container in order to provide tacit notice to the user that the cap is not intended to be re-used. The user is thereby encouraged to leave the used exit conduit coupled to the container between uses to provide a seal for remaining components in the barrels.

U.S. Pat. No. 4,974,756 (also assigned to the assignee of the present invention) also describes a double barrel dispensing container assembly with a cap. In this reference, the cap includes two side-by-side outwardly projecting closure portions for simultaneously moving within and closing both outlets of a double barrel container when the cap is connected to the container. The cap includes two protruding orienting sections for orienting the cap relative to the container as the cap is connected to the container. However, it is sometimes difficult to replace the cap after use because of the difficulty in displacing the components present at the outlet openings when the protruding closure portions are moved into the outlet openings.

SUMMARY OF THE INVENTION

One aspect of the present invention is directed toward a dispensing container assembly that comprises a dispensing container having a protruding outlet with an outlet opening and an outer surface surrounding the outlet opening. The assembly also includes a cap for covering the outlet. The container and the cap each include releasable coupling structure for coupling the cap to the container as the cap is moved in a certain direction across the outlet opening toward a closed position. The cap includes a body and also includes a gasket in compression against the outer surface when the cap is in the closed position. One of the container and the body includes a bearing surface portion, and the other of the container and the body includes a cam portion engagable with the bearing surface portion for retaining the body a first distance from the outer surface in a direction laterally of the certain direction as the cap is moved in the certain direction across the outlet opening. The cam portion and the bearing surface portion have a configuration that enable the body to move closer to the outer surface than the first distance mentioned above when the cap is in the closed position in order to increase the compression of the gasket against the outer surface.

Another embodiment of the present invention is directed toward a dispensing container assembly that comprises a dispensing container having a protruding outlet with an outlet opening and an outer surface surrounding the outlet opening. The assembly also includes a cap for covering the outlet. The container and the cap each include releasable coupling structure for coupling the cap to the container as the cap is moved in a direction across the outlet opening toward a closed position. The cap includes a gasket in compression against the outer surface when the cap is in the closed position. The cap also includes a cam portion located next to the gasket, and the cam portion has an apex for engagement with the outer surface as the cap is moved in a direction across the outlet opening. The apex is disengaged from the outer surface when the cap is in the closed position in order to increase the compression of the gasket against the outer surface.

The cam portion is an advantage, in that the cam portion relieves pressure on the gasket as the cap is sliding across the outlet opening. If desired, the cam portion may be dimensioned to enable the cap to snap in place when closed. The snap action provides feedback to the user that the cap is properly closed and also hinders inadvertent detachment of the cap during shipping or handling.

Anther aspect of the present invention is directed toward a dispensing container assembly that comprises a dispensing container having a first chamber and a second chamber. The container includes a first outlet opening in communication with the first chamber and a second outlet opening in communication with the second chamber. The first outlet opening is located adjacent the second outlet opening. The dispensing container assembly also includes a cap for covering the first outlet opening and the second outlet opening. The container and the cap each include releasable coupling structure for coupling the cap to the container as the cap is slidably moved in a direction across the first outlet opening and the second outlet opening toward a closed position. The cap has a first closure portion and a second closure portion for closing the first outlet opening and the second outlet opening respectively. At least one of the container and the cap includes an orienting section for substantially preventing the cap from coupling to the container in an orientation wherein the first closure portion slides across the second outlet opening and the second closure portion slides across the first outlet opening.

The orienting section substantially reduces the likelihood of cross-contamination of components from one chamber to the other. If, for example, a small, residual amount of a component that is stored in one chamber is present on one of the closure portions, the orienting section will prevent such residual amount from being inadvertently placed over the outlet opening of the other chamber and being smeared into such chamber. As a result, cross-contamination and possible premature curing of the components can be avoided.

BRIEF DESCRIPTION OF THE DRAWINGS

FIG. 5 is a front side elevational view of a container of the assembly;

FIG. 6 is a plan view of the container illustrated in FIG. 5; and

FIG. 7 is an enlarged, fragmentary, right side elevational view of the container depicted in FIGS. 5–6 along with the cap that is shown in FIGS. 1–4, wherein the cap is coupled to the container to close a protruding outlet of the container.

BRIEF DESCRIPTION OF THE PREFERRED EMBODIMENTS

Figure 1:
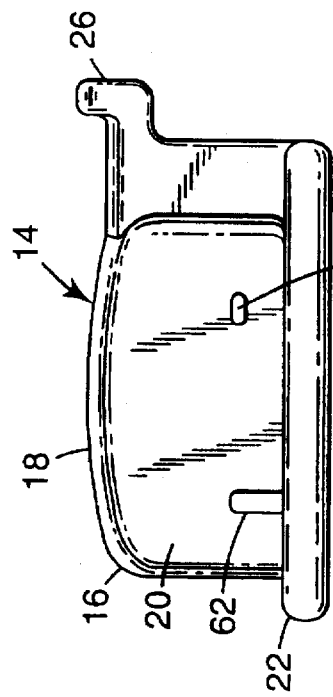
FIG. 1 is a top, front, right side perspective view of a cap for a container and sliding cap assembly according to one embodiment of the present invention.

A dispensing container and sliding cap assembly constructed in accordance with the principles of the present invention is partially illustrated in FIG. 7 and is broadly designated by the numeral 10. The assembly 10 includes a double-barrel dispensing cartridge or container 12 that is shown alone in FIGS. 5–6, and a sliding cap 14 that is shown alone in FIGS. 1–4.

The cap 14 includes a body 16 that is preferably integrally molded of acetal resin such as is sold under the tradename DELRIN 500 (from DuPont). The body 16 includes a top section 18, a sidewall section 20 that is connected to the top section 18 and a lip section 22 that extends along and is integrally connected to the bottom of the sidewall section 20. The lip section 22 includes two flange portions that extend outwardly and away from each other in opposite directions. The sidewall section 20 has a generally "C"-shaped configuration when viewed toward a horizontal cross-section. The top section 18 and the sidewall section 20 are extended on one side of the body 16 and together present an inverted, generally U-shaped opening 24.

An elongated bar 26 extends along the top of the opening 24 and is integrally connected to the top section 18. The bar 26 presents a convenient, comfortable surface for pushing the cap 14 off of the container 12 when desired.

Turning now to FIGS. 5 and 6, the container 12 includes a first cylindrical barrel 28 and a second cylindrical barrel 30 that is integrally connected to the first barrel 28 in side-by-side relation. Both of the barrels 28, 30 have an elongated, cylindrical inner chamber with a rear circular opening. The opening of each chamber is closed by a piston for ejecting components from the respective chambers when desired. Preferably, the longitudinal axes of the chambers of the barrels 28, 30 are parallel to each other.

The container 12 also includes a rear, generally rectangular flange 32 that surrounds the rear opening of the barrels 28, 30. A recess 34 is located on each side of the flange 32. The flange 32 has a webbed construction that comprises a front plate surrounding a rear end portion of the barrels 28, 30, a generally rectangular structure extending around the periphery of the flange 32 and two circular structures that are integrally joined to (and form part of) the end portions of the barrels 28, 30. The circular structures are also integrally joined to adjacent portions of the generally rectangular structure and the front plate.

A front end of the container 12 opposite the end containing the flange 32 includes a protruding outlet 36 having a generally cylindrical configuration. The outlet 36 includes a first outlet opening 38 (FIGS. 5 and 6) that is in communication with the chamber within the first barrel 28 and a second outlet opening 40 that is in communication with the chamber of the second barrel 30. The outlet openings 38, 40 have a generally "D"-shaped configuration as illustrated in FIG. 6 and are separated from each other by a dividing wall.

The outer end of the protruding outlet 36 has a flat outer surface 42 that includes an annular wall portion as well as the outer end of the dividing wall. The outer end of the dividing wall is coplanar with the annular wall portion.

The outlet 36 is located between two "L"-shaped ears 44 that are adapted to releasably engage a plate of a static mixing assembly and form a bayonet-style coupling. Suitable static mixers are described in, for example, U.S. Pat. No. 4,538,920 as well as pending U.S. patent application Ser. No. 08/547,451 entitled "Dual Chamber Cartridge Dispensing System for Dental Material" and filed on even date herewith. The ears 44 are also adapted to engage the two flange portions of the lip section 22 of the cap 14 as described in more detail below.

The container 12 is preferably integrally molded of an amorphous polyolefin such as is sold under the tradename "ZEONEX" grade 480 (from Nippon Zeon Co., Ltd., Tokyo, Japan). Alternatively, the cartridge can be made of a polyethylene such as is sold under the tradename "ALATHON H5618" (from Occidental Chemical Corporation, Dallas, Tex.) or a polypropylene resin such as is sold under the tradename "FINA 3467" (from Fina Oil and Chemical Company, Deer Park, Tex.). Further information regarding the cartridge material can be obtained in U.S. Pat. No. 5,624,260 entitled "Delivery System for Aqueous Paste Dental Materials", the disclosure of which is expressly incorporated by reference herein.

Figure 3:
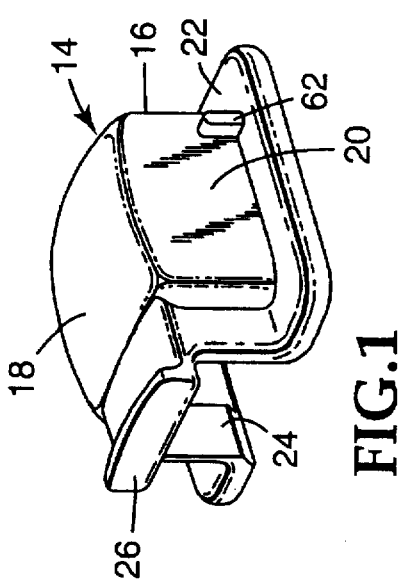
FIG. 3 is an enlarged bottom view of the cap shown in FIG. 1.

Referring now to FIG. 3, the top section 18 of the cap 14 includes a circular cavity that is surrounded by an annular wall 46. A gasket 48 is received in the cavity and is made of a resilient, compressible material that preferably is impermeable to the passage of water and does not exhibit a compression set. Suitable materials for the gasket 48 include buna-N synthetic rubber (such as "WARCO WHITE" buna-N gasket material, Style No. 55-P-146, 55 durometer hardness, 0.06 in. (1.5 mm) thick, from Western America Rubber Company). The gasket 48 is retained in place in the cavity by a diametrical interference fit and also by an adhesive (such as Scotch™ brand adhesive transfer tape, No. 9924XL; from 3M).

The lip section 22 of the cap 14 and the ears 44 of the container 12 function as releasable coupling structure for coupling the cap 14 to the container 12 as the cap 14 is moved across the outlet openings 38, 40 toward a closed position. The closed position of the cap 14 is illustrated in FIG. 7, and the movement of the cap 14 toward the closed position occurs in a direction toward the left when viewing FIG. 7.

The top section 18 of the cap 14 includes a cam portion 50 (FIGS. 3 and 7) that is engagable with the outer surface 42 of the outlet 36 as the cap 14 is moved in a direction toward the closed position, or moved in the opposite direction toward a disengaged position. The cam portion 50 includes two oppositely inclined flat ramps that are each inclined at an angle of 30° from horizontal (viewing FIG. 7). The ramps meet along a linear apex 52. The apex 52 engages the outer surface 42 as the cap 14 is moved across the outlet 36 but is disengaged from the outer surface 42 when the cap 14 is in its fully closed position.

The outer surface 42 functions as a bearing surface portion for engagement with the cam portion 50. As the cap 14 is moved toward the closed position, the cam portion 50 engages the outer surface 42 and shifts the body 16 in a direction away from the outer surface 42 (and in an upwardly direction viewing FIG. 7) as the cap 14 is moved toward the closed position. Once the apex 52 contacts the outer surface 42, the apex 52 retains the top section 18 a first, certain distance away from the outer surface 42 in a direction laterally of the direction of movement of the cap 14 toward its closed position.

Preferably, the lip section 22 is more yielding than the ears 44. As a result, the lip section 22 flexes somewhat as the cap 14 is moved toward a closed position in order to enable the cam portion 50 to shift the top section 18 away from the outer surface 42. The ears 44 therefore provide a fixed, stable coupling structure for a static mixer when it is desired to dispense material from the container 12.

As the cap 14 moves toward its closed position, the apex 52 slides along the outer surface 42 until it reaches the left side of the outlet 36 (viewing FIG. 7). As the cap 14 continues to move toward its closed position, the apex 52 moves beyond the outer surface 42 and the shape of the cam portion 50 enables the top section 18 of the body 16 to move laterally toward the outer surface 42 (or in a downwardly direction viewing FIG. 7).

The configuration of the cam portion 50 and the bearing surface portion or outer surface 42 enable the cap 14 to be moved toward its closed position without undue pressure on the gasket 48. If, for example, the apex 52 is in the same horizontal plane as the bottom of the gasket 48 viewing FIG. 7 when the gasket 48 is uncompressed, the gasket will readily slide across the outer surface 42, and the circular periphery of the gasket 48 will normally not catch against the side of the outlet 36 (which might otherwise cause the gasket 48 to fold over, tear or become dislodged from the cavity of the cap 14).

Once the cap 14 is fully closed, however, the configuration of the cam portion 50 and the outer surface 42 are such that the apex 52 has disengaged the outer surface 42, and the outer surface 42 is instead in contact only with the bottom of the gasket 48. At such time, the top section 18, being now somewhat closer to the outer surface 42, compresses the gasket 48 to a greater degree than the compression, if any, of the gasket 48 during the time that the apex 52 engages the outer surface 42. Such increased compression of the gasket 48 provides a better seal between material in the chambers of the barrels 28, 30 and the atmosphere.

The body 16 optionally includes an orienting section 54 (FIGS. 2 and 4) which, in the embodiment shown, comprises an outwardly extending finger. The orienting section 54 is located to clear the ear 44 that is shown on the right-hand side of FIGS. 5 and 6 when the cap 14 is moved toward its closed position. However, if the cap 14 is moved toward the outlet 36 from the opposite side of the container 12, the orienting section 54 comes into contact with a projecting stop 56 that is integrally connected to the ear 44 located on the left-hand side of FIGS. 5 and 6. The stop 56 and the orienting section 54 consequently allow the cap 14 to be closed only when the cap 14 approaches one side of the container 12 and not the other.

The gasket 48 has a first closure portion 58 (FIG. 3) for closing the first outlet opening 38 (FIGS. 5-6) of the container 12 and a second closure portion 60 for closing the second outlet opening 40 of the container 12. The orienting section 54 (FIGS. 2 and 4) insures that the first closure portion 58 passes only over the first outlet opening 38 and the second closure portion 60 passes only over the second outlet opening 40. The orienting section 54 prevents the first closure portion 58 from sliding across the second outlet opening 40 and the second closure portion 60 from sliding across the first outlet opening 38. As such, the orienting section 54 prohibits any residual amount of component on the gasket 48 from one chamber from contacting the component in the other chamber when the cap 14 is closed.

Figure 2:
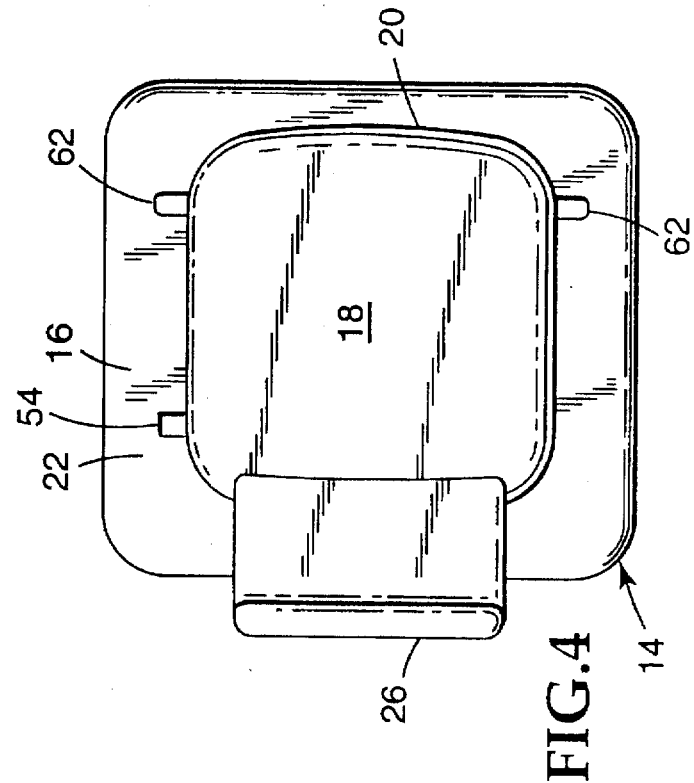
FIG. 2 is an enlarged left side elevational view of the cap shown in FIG. 1.
Figure 4:
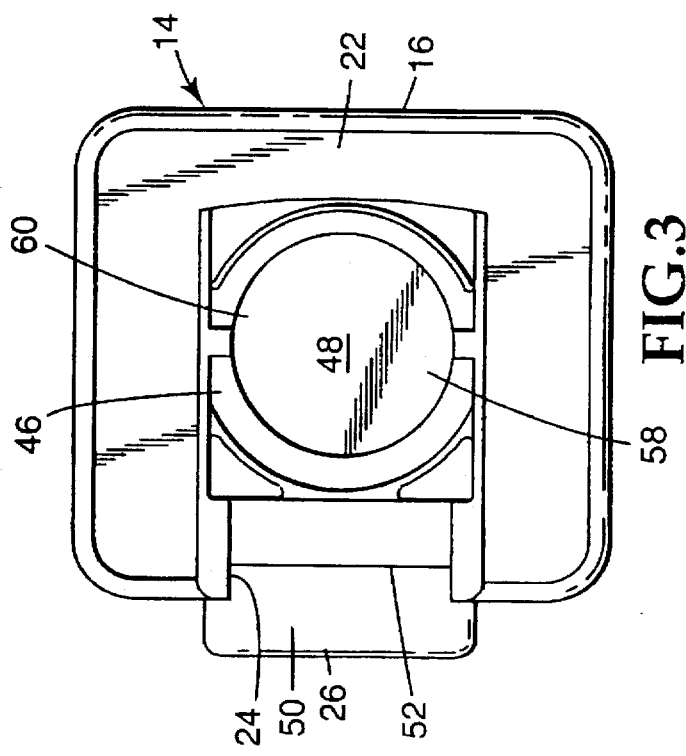
FIG. 4 is an enlarged plan view of the cap shown in FIG. 1.

The cap 14 additionally includes a pair of stop tabs 62 that are illustrated in FIGS. 1, 2 and 4. When the cap 14 is in its fully closed position, the tabs 62 engage the ears 44 to prevent further movement of the cap 14 in a direction center of the side of FIG. 7 and to insure that the center of the gasket 48 remains aligned over the center of the outlet 36.

Components in the chambers can be dispensed once the cap 14 is removed from the container 12 and the container 12 is received in an applicator. Suitable manual applicators are described in the aforementioned U.S. patent application entitled "Dual Chamber Cartridge Dispensing System for Dental Material." Other applicators, including motorized, pneumatic or hydraulic applicators may also be used.

Many other variations and additions to the presently preferred embodiment set out above are possible and within the scope of the invention. For example, the cam portion 50 may be located on other areas of the body 16 (for example, on the lip section 22) or alternatively may be located on the container 12. Moreover, the outlet openings 38, 40 may be spaced apart from each other or have a shape other than that which is shown. Other types of coupling structures are also possible. As such, the scope of the invention should not be limited to the construction above that is set out in detail, but only by a fair reading of the claims that follow along with their equivalents.

We claim:

1. A dispensing container assembly comprising:
   a dispensing container having a protruding outlet with an outlet opening and an outer surface surrounding said outlet opening; and
   a cap for covering said outlet, said container and said cap each including releasable coupling structure for coupling said cap to said container as said cap is moved in a certain direction across said outlet opening toward a closed position, said cap including a body, said cap including a gasket in compression against said outer surface when said cap is in said closed position, said body including a cam portion engagable with said outer surface for retaining said body a first distance from said outer surface in a direction laterally of said certain direction as said cap is moved in said certain direction across said outlet opening, wherein said cam portion includes a ramp portion that enables said body to move closer to said outer surface than said first distance when said cap is in said closed position in order to increase the compression of said gasket against said outer surface, wherein said releasable coupling structure of said cap includes a pair of flange portions that extend outwardly in directions away from each other, and wherein said releasable coupling structure of said container includes a pair of ears for engagement with said flange portions.

2. The assembly of claim 1, wherein said outlet also includes a second outlet opening.

3. The assembly of claim 1, wherein said cam portion includes an apex that is disengaged from said outer surface when said cap is in said closed position.

4. The assembly of claim 1, wherein said outlet also includes a second outlet opening and wherein said gasket includes a first closure portion and a second closure portion, said cap also including an orienting section for substantially preventing said cap from coupling to said container in an orientation wherein said first closure portion slides across said second outlet opening.

5. A dispensing container assembly comprising:
   a dispensing container having a protruding outlet with an outlet opening and an outer surface surrounding said outlet opening; and
   a cap for covering said outlet, said container and said cap each including releasable coupling structure for coupling said cap to said container as said cap is moved in a direction across said outlet opening toward a closed position, said cap including a gasket in compression against said outer surface when said cap is in said closed position, said cap also including a cam portion located next to said gasket, said cam portion having an apex for engagement with said outer surface as said cap is moved in a direction across said outlet opening, said apex being disengaged from said outer surface when said cap is in said closed position in order to increase the compression of said gasket against said outer surface, wherein said releasable coupling structure of said cap includes a pair of flange portions that extend outwardly in directions away from each other, and wherein said releasable coupling structure of said container includes a pair of ears for engagement with said flange portions.

6. The assembly of claim 5, wherein said outlet includes a second outlet opening.

7. The assembly of claim 5, wherein said cam portion includes a pair of oppositely inclined ramp portions that join at said apex.

8. The assembly of claim 5, wherein said outlet includes a second outlet opening, and wherein said cap includes a first closure portion and a second closure portion, and wherein at least one of said container and said cap includes an orienting section for substantially preventing said cap from coupling to said container in an orientation wherein said first closure portion slides across said second outlet opening.

9. A dispensing container assembly comprising:
   a dispensing container having a first chamber and a second chamber, said container including a first outlet opening in communication with said first chamber and a second outlet opening in communication with said second chamber, said first outlet opening located adjacent said second outlet opening; and
   a cap for covering said first outlet opening and said second outlet opening, said container and said cap each including releasable coupling structure for coupling said cap to said container as said cap is slidably moved in a direction across said first outlet opening and said second outlet opening toward a closed position, said cap having a first closure portion and a second closure portion for closing said first outlet opening and said second outlet opening respectively, at least one of said container and said cap including an orienting section for substantially preventing said cap from coupling to said container in an orientation wherein said first closure portion slides across said second outlet opening.

10. The assembly of claim 9, wherein said orienting section comprises an outwardly extending finger.

11. The assembly of claim 9, wherein said cap includes a body and a gasket connected to said body, and wherein said gasket includes said first closure portion and said second closure portion.

12. The assembly of claim 11, wherein one of said cap and said container includes a bearing surface portion and the other of said cap and said container include a cam portion engagable with said bearing surface portion when said cap is moved away from said closed position for shifting said body in a direction laterally away from said first outlet opening and said second outlet opening.

13. The assembly of claim 9, wherein said cap includes said orienting section, and wherein said orienting section contacts said releasable coupling structure of said container when an attempt is made to couple said cap to said container in an orientation wherein said first closure portion slides across said second outlet opening.

14. The assembly of claim 13, wherein said releasable coupling structure of said container includes a generally "L"-shaped ear.

15. The assembly of claim 14, wherein said releasable coupling structure of said cap includes an outwardly extending lip section for mating engagement with said ear.

* * * * *